United States Patent [19]

Greenlee

[11] Patent Number: 5,274,550

[45] Date of Patent: Dec. 28, 1993

[54] BLOOD ALCOHOL LEVEL DETERMINING DEVICE

[76] Inventor: Robert J. Greenlee, 510 Eau Claire Blvd., Wausau, Wis. 54401

[21] Appl. No.: 761,282

[22] Filed: Sep. 17, 1991

[51] Int. Cl.⁵ .............................................. G06F 15/00
[52] U.S. Cl. ............................ 364/413.09; 364/413.11
[58] Field of Search ..................... 364/413.09, 413.11; 73/23.3

[56] References Cited

U.S. PATENT DOCUMENTS

| | | | |
|---|---|---|---|
| 4,071,891 | 1/1978 | Barrows | 364/416 |
| 4,095,274 | 6/1978 | Gordon | 364/715 |
| 4,192,006 | 3/1980 | Hausdorff | 364/715 |
| 4,321,674 | 3/1982 | Krames et al. | 364/413 |
| 4,446,528 | 5/1984 | Marmon | 364/709 |
| 4,654,215 | 3/1987 | Yamada et al. | 426/17 |
| 4,678,057 | 7/1987 | Elfman et al. | 180/272 |
| 4,692,414 | 9/1987 | Yamada et al. | 435/291 |
| 4,709,331 | 11/1987 | Barkett et al. | 364/413 |
| 4,715,386 | 12/1987 | Martin | 128/733 |
| 4,749,553 | 6/1988 | Lopez et al. | 422/84 |
| 4,775,780 | 10/1988 | Ross, Jr. | 235/89 |
| 4,809,810 | 3/1989 | Elfman et al. | 180/272 |
| 4,822,337 | 4/1989 | Newhouse et al. | 604/50 |
| 5,157,601 | 10/1992 | Jones et al. | 364/413.11 |

OTHER PUBLICATIONS

ATS-CLE, Defending Speeding and Drunk Driving Cases Jun., 1981.

*Primary Examiner*—Roy N. Envall, Jr.
*Assistant Examiner*—Ari M. Bai
*Attorney, Agent, or Firm*—Michael, Best & Friedrich

[57] ABSTRACT

A blood alcohol level determining device for calculating the blood alcohol level of a person, the blood alcohol level determining device comprising: first memory structure for storing characteristic information regarding the person; second memory structure for storing characteristic information regarding an alcoholic beverage; human interface structure for receiving, from a human operator of the device, information regarding the characteristics of the person and the characteristics of an alcoholic beverage, the interface structure communicating with the first and second memory structure; clock structure for measuring time; and structure communicating with the clock structure, with the first memory structure, and with the second memory structure, for calculating a blood alcohol level for the person based on the characteristics of the alcoholic beverage, the characteristics of the person, and time measured by the clock structure.

14 Claims, 9 Drawing Sheets

BLOOD ALCOHOL LEVEL DETERMINING DEVICE

BACKGROUND OF THE INVENTION

The invention relates to blood alcohol level determining devices.

A known blood alcohol level determining device requires a person to blow into the device. An analysis of the person's breath is performed by the device, and blood alcohol level is then calculated by the device based on that breath analysis. See, for example, U.S. Pat. No. 4,809,810, issued to Elfman et al. on Mar. 7, 1989, U.S. Pat. No. 4,749,553, issued to Lopez et al. on Jun. 7, 1988.

Another known blood alcohol level determining device is disclosed in U.S. Pat. No. 4,775,780, issued to Ross, Jr. on Oct. 4, 1988. That device comprises a mechanical balance board. Weights representing alcohol consumed are placed on one side of the board, weights representing alcohol oxidized over a period of time are placed on the other side of the board, and the tilt of the board indicates blood alcohol level.

SUMMARY OF THE INVENTION

The invention provides a blood alcohol level determining device that calculates a blood alcohol level for a person based on. stored characteristic information pertaining to that person (e.g. weight, sex), input information pertaining to the character of (an) alcoholic beverage(s) consumed, and elapsed time.

One embodiment of the invention provides a device that calculates a blood alcohol level for at least one, and preferably two persons. Information regarding the characteristics of each of the persons (i.e., sex, and weight) are initially entered into the device. Every time an alcoholic beverage is ordered by either of the two people, a user (usually one of the two people, or possibly someone else, i.e., a friend, a bartender, or a host) presses appropriate keys on the device and a calculation of a blood alcohol level is made. The result of the calculation is displayed to the user, and if the calculated blood alcohol level for the relevant person is in excess of a user selectable predetermined level, i.e., a level chosen by a State as a maximum level over which someone is too intoxicated to legally drive (e.g. 0.10% in some states), then an alarm in the device is turned on. Preferably the device includes both an audible, and a visual alarm, both of which are turned on if the calculated blood alcohol level for the relevant person is in excess of the predetermined level.

Other features and advantages of the invention will become apparent to those skilled in the art upon review of the following detailed description, claims and drawings.

DETAILED DESCRIPTION OF THE PREFERRED EMBODIMENT OF THE INVENTION

Figure 1:
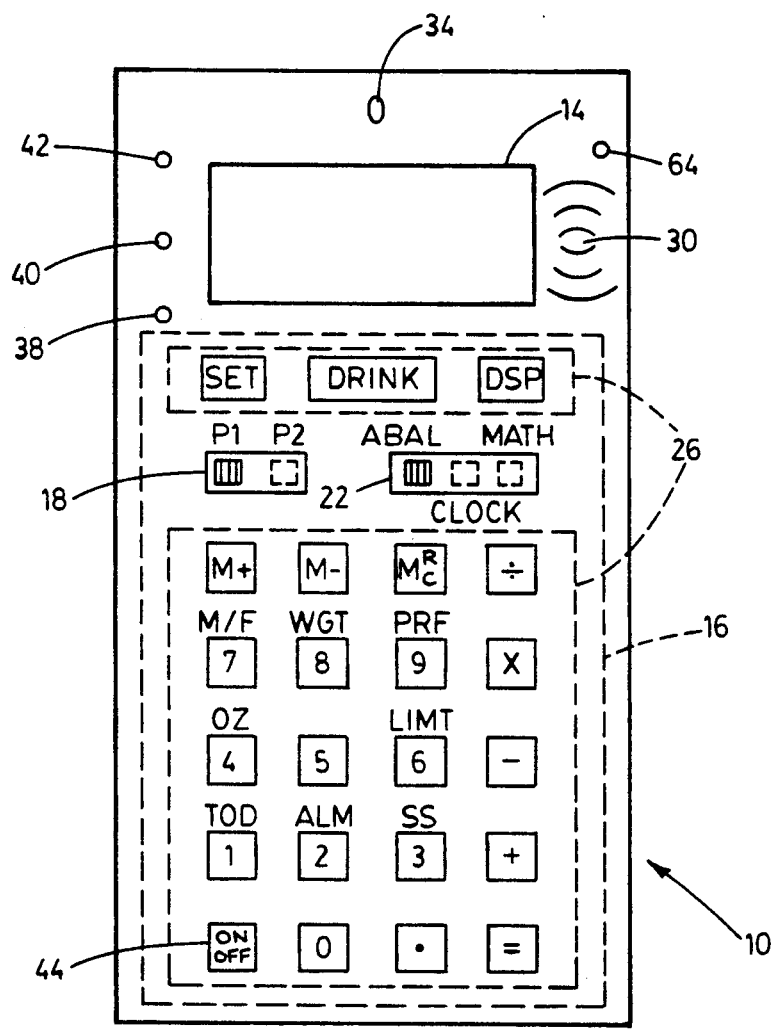
FIG. 1 is a top plan view of a blood alcohol level determining device embodying various of the features of the invention.

Shown in FIG. 1 is a blood alcohol level determining device 10 embodying various of the features of the invention. The device 10 is generally of the configuration of a hand held calculator. The device 10 includes an alphanumeric display 14. The device 10 further includes human interface means 16 comprising a two position switch 18 movable between a first position, marked "P1" (representing a first person whose blood alcohol level is being monitored), and a second position, marked "P2" (representing a second person whose blood alcohol level is being monitored), and a three position "mode" switch 22 movable between a first position, marked "ABAL", a second position, marked "CLOCK", and a third position, marked "MATH". The human interface means 16 further includes a keypad 26 defined by a plurality of momentary switches or keys including a decimal point key ("."), an addition key ("+"), a subtraction key ("−"), a multiplication key ("×"), a division key ("÷"), an equals key ("="), an add to memory key ("M+"), a subtract from memory key ("M−"), a memory recall/memory clear key ("M$_C$$^R$"), a key marked "SET", a key marked "DRINK", and a key marked "DSP". The keypad further includes keys numerical keys marked from "0" through "9". Some of the keys of the keyboard 26 perform different functions, which will be described below, depending on which position the mode switch 22 is in. In the illustrated embodiment, the key marked "1" is also marked "TOD", the key marked "2" is also marked "ALM", the key marked "3" is also marked "SS", the key marked "4" is also marked "OZ", the key marked "6" is also marked "LIMT", the key marked "7" is also marked "M/F", the key marked "8" is also marked "WGT", and the key marked "9" is also marked "PRF". The device 10 further includes an audible alarm or indicator 30, an aperture 34 for receiving a keychain; and visual indicators 38, 40, and 42. Preferably, the visual indicator 38 is a green visual indicator, the visual indicator 40 is a yellow or amber visual indicator, and the visual indicator 42 is a red visual indicator. The visual indicators 38, 40, and 42 can comprise light emitting diodes. The device 10 further includes an on/off switch 44 which can be in the form of a key on the keyboard 26, or which can be in the form of a switch similar in type to the switch 18.

Figure 2:
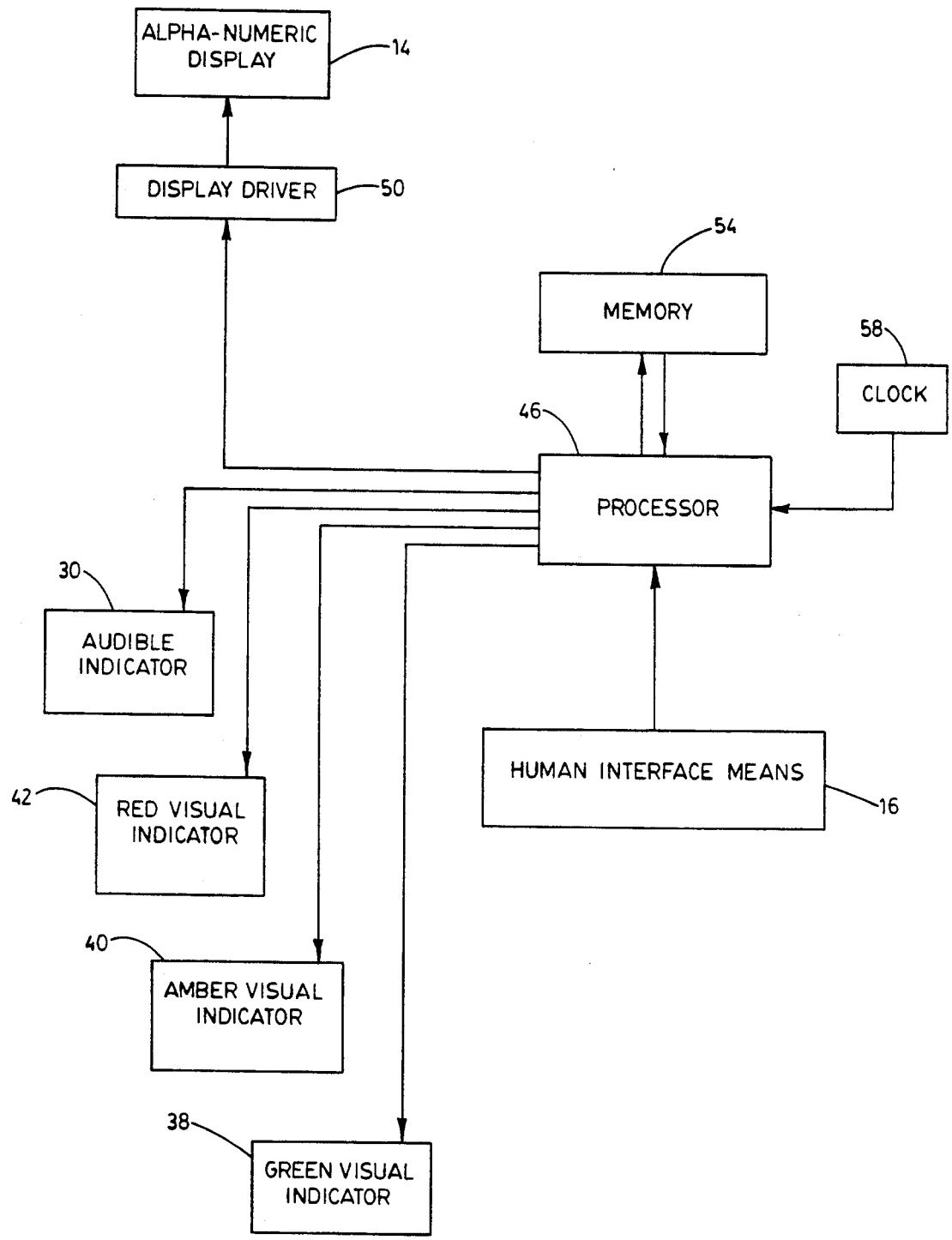
FIG. 2 is a block diagram of the circuitry of the blood alcohol level determining device shown in FIG. 1.
Figure 3A:
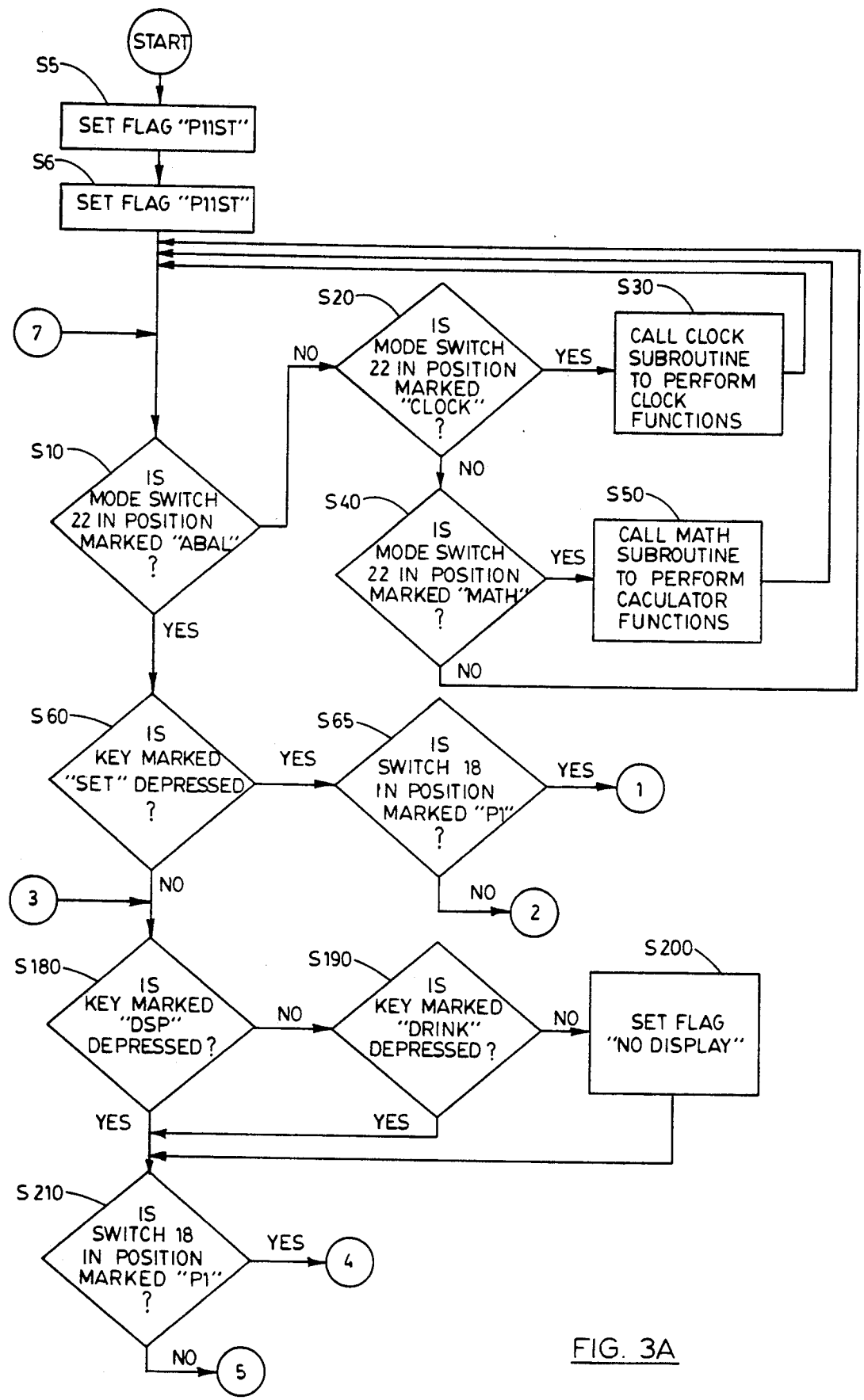
FIGS. 3A-G is a flowchart illustrating a sequence of steps followed by the blood alcohol level determining device shown in FIG. 1.
Figure 3B:
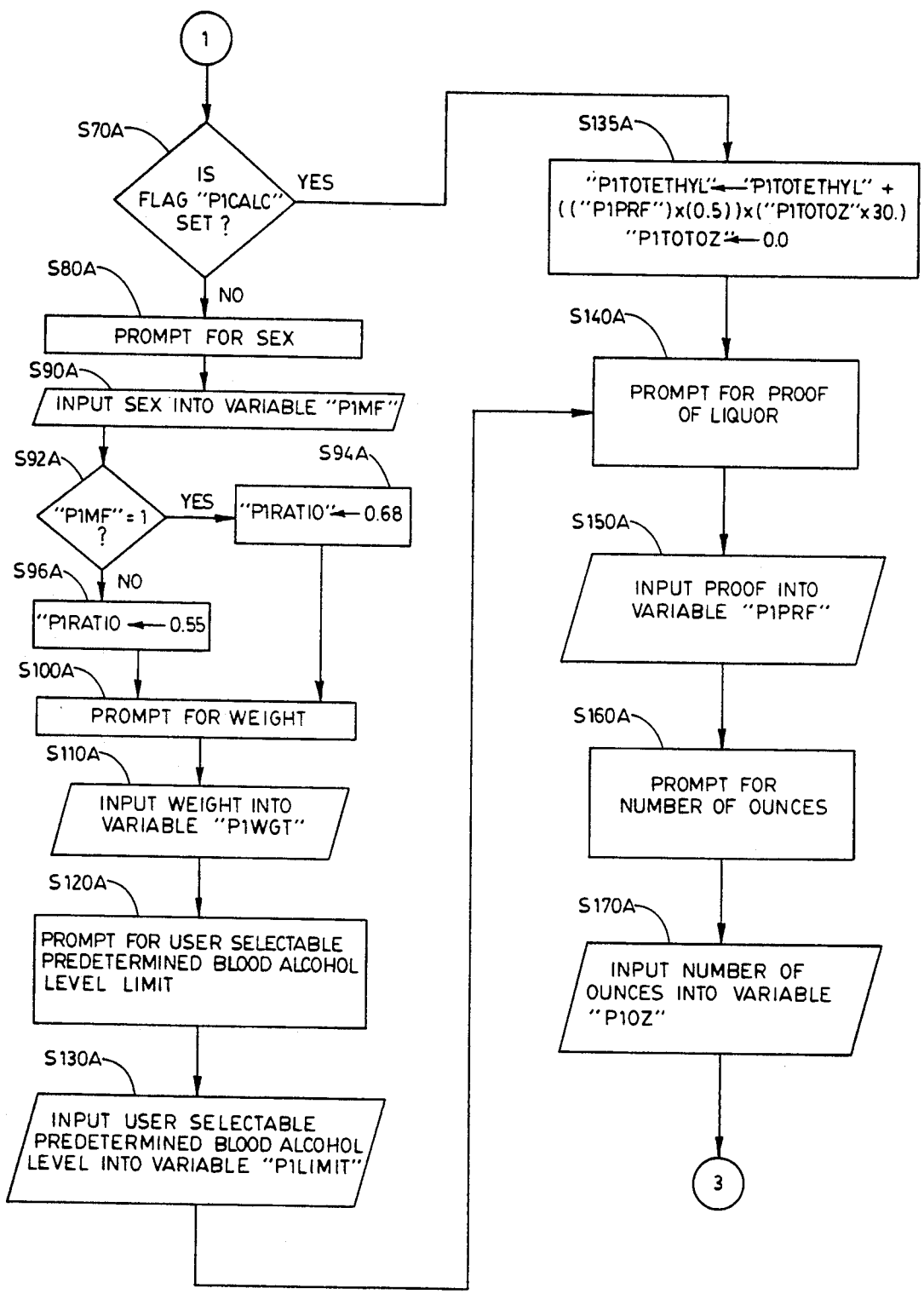
Figure 3C:
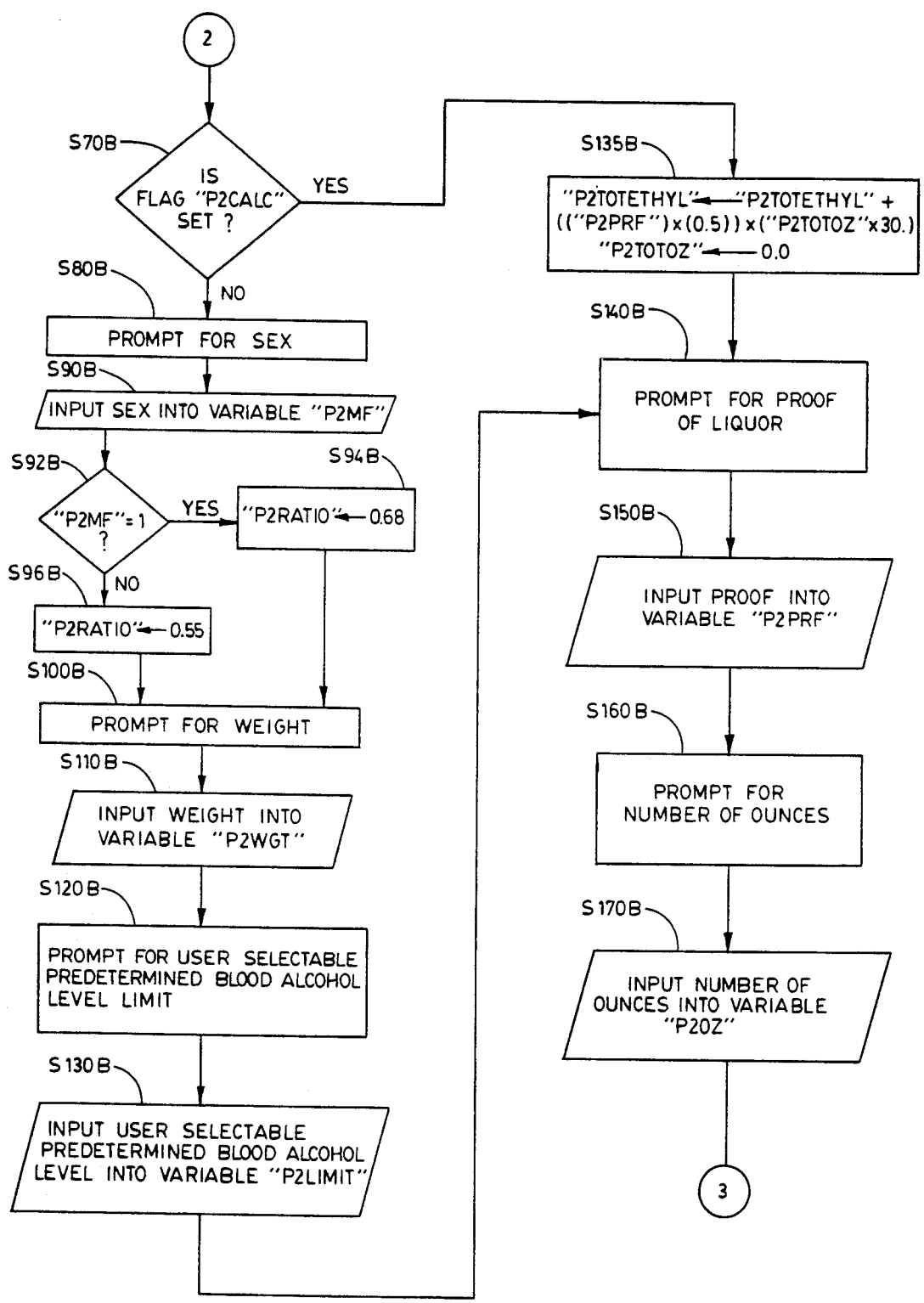
Figure 3D:
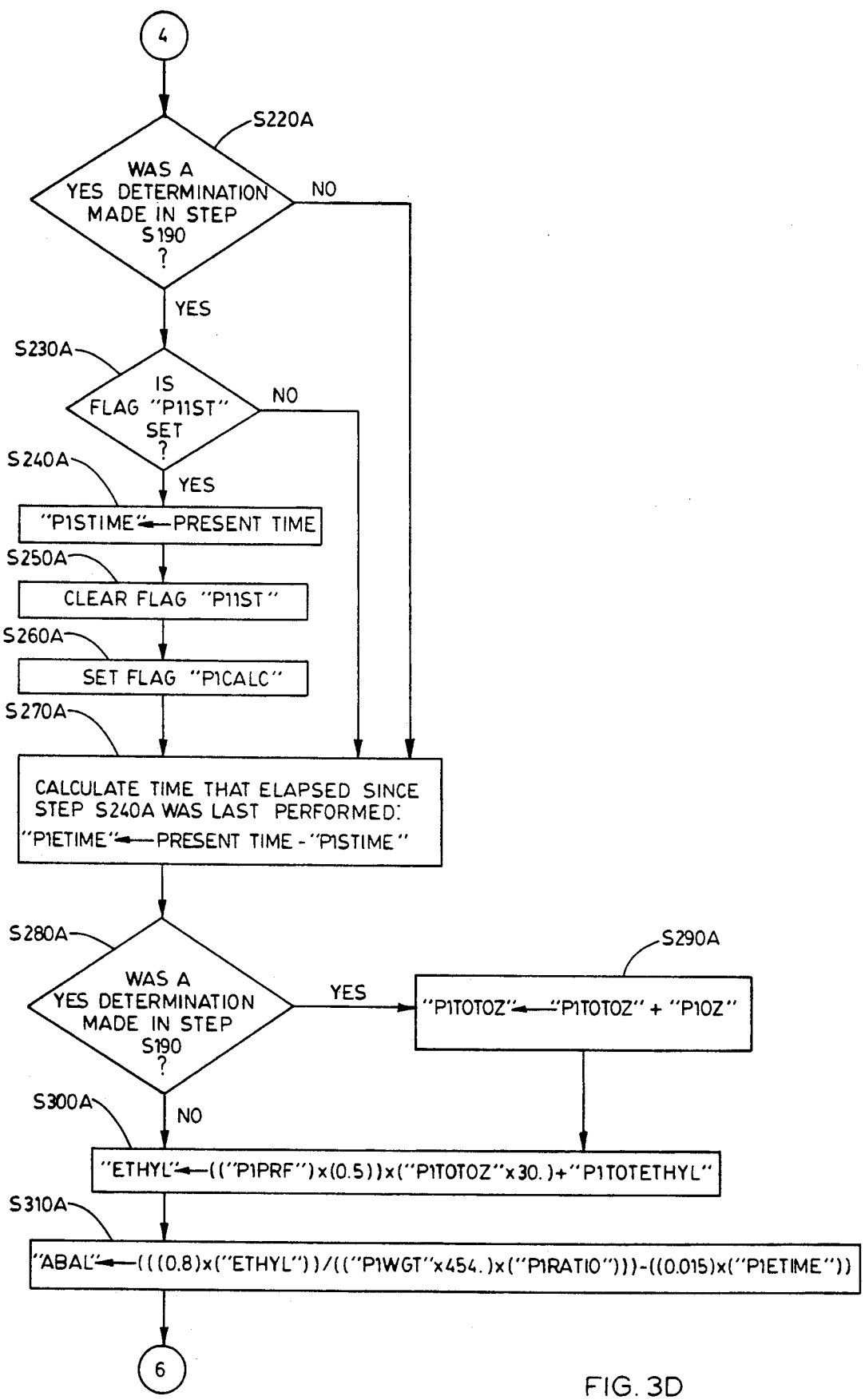
Figure 3E:
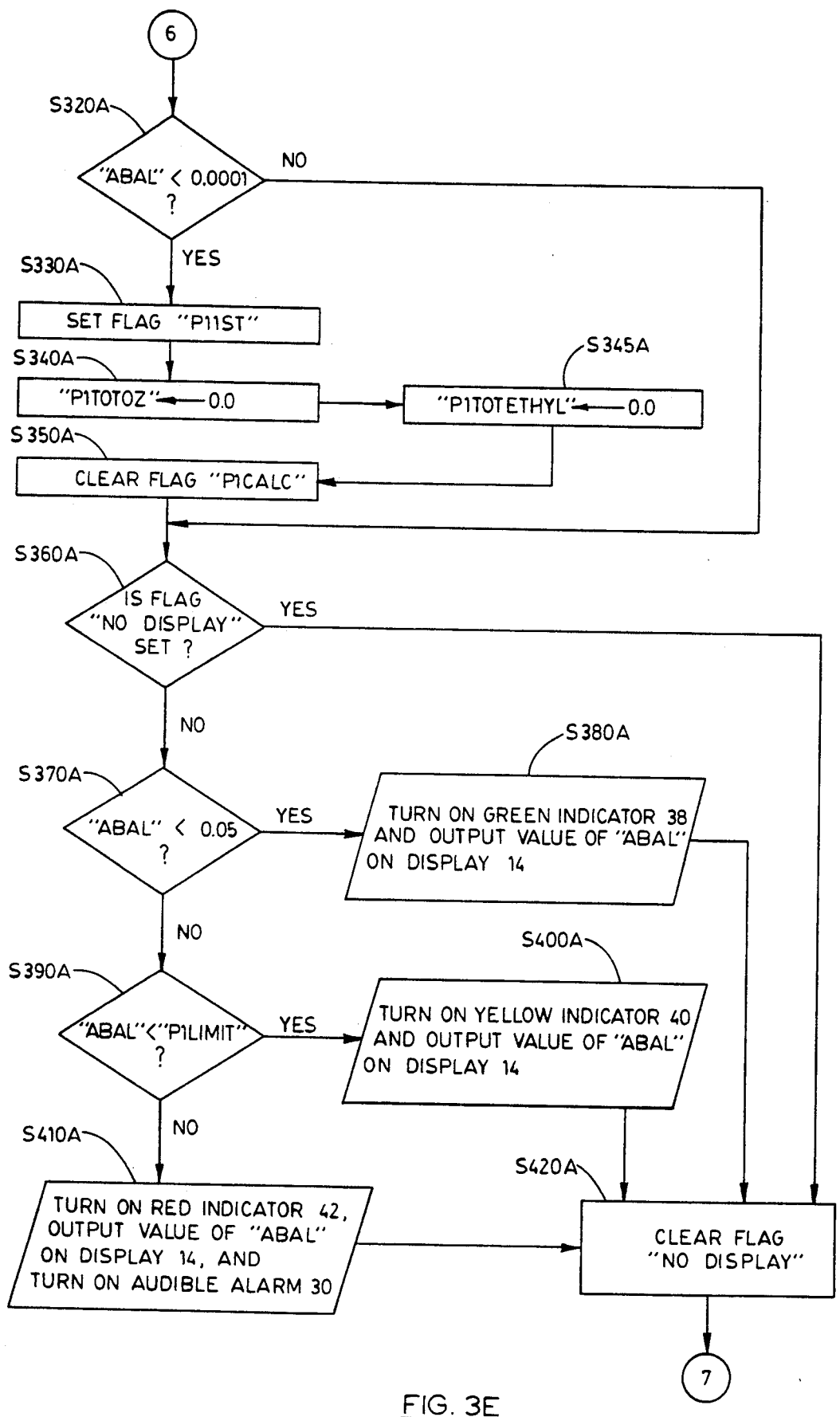
Figure 3F:
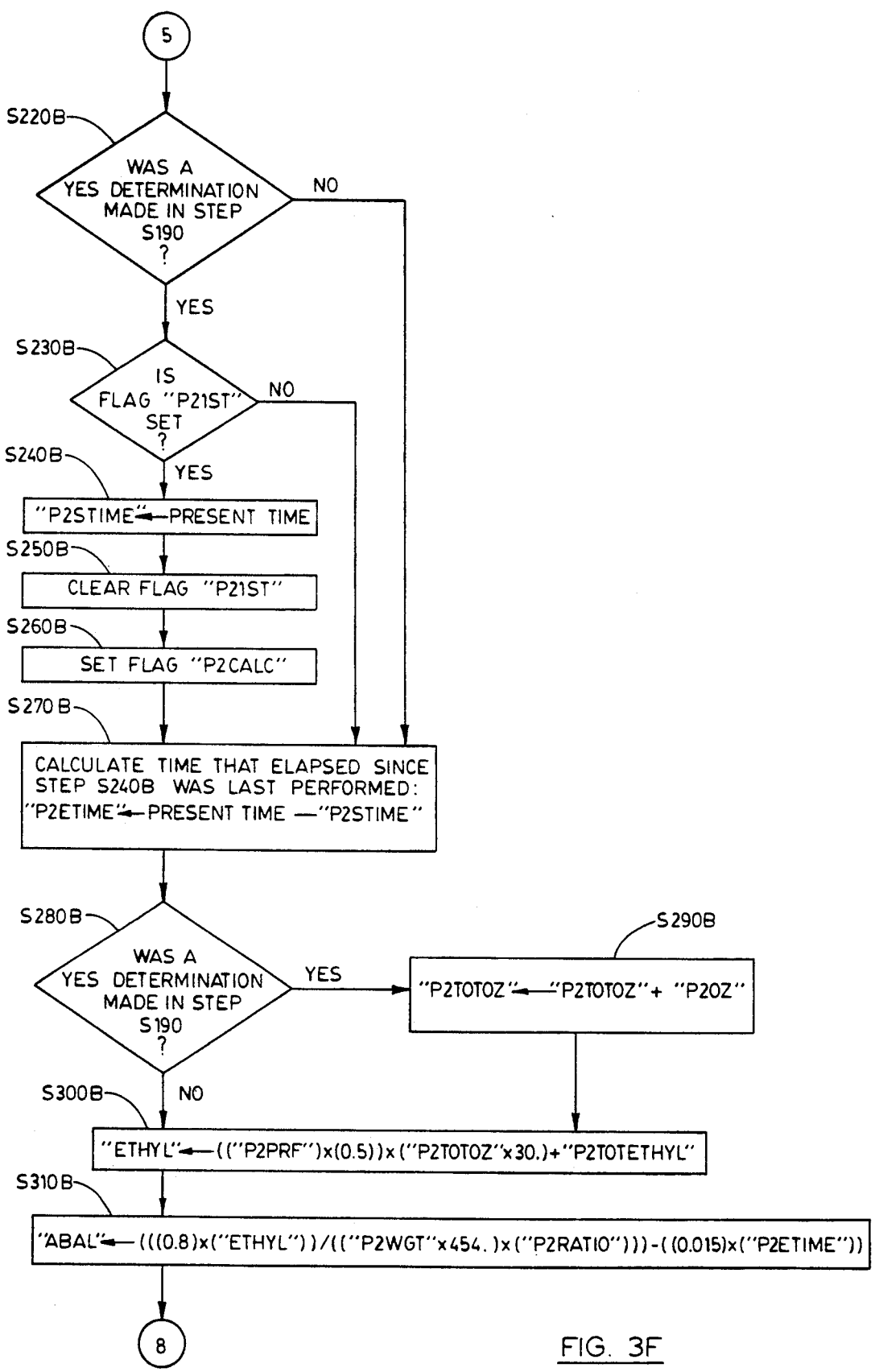
Figure 3G:
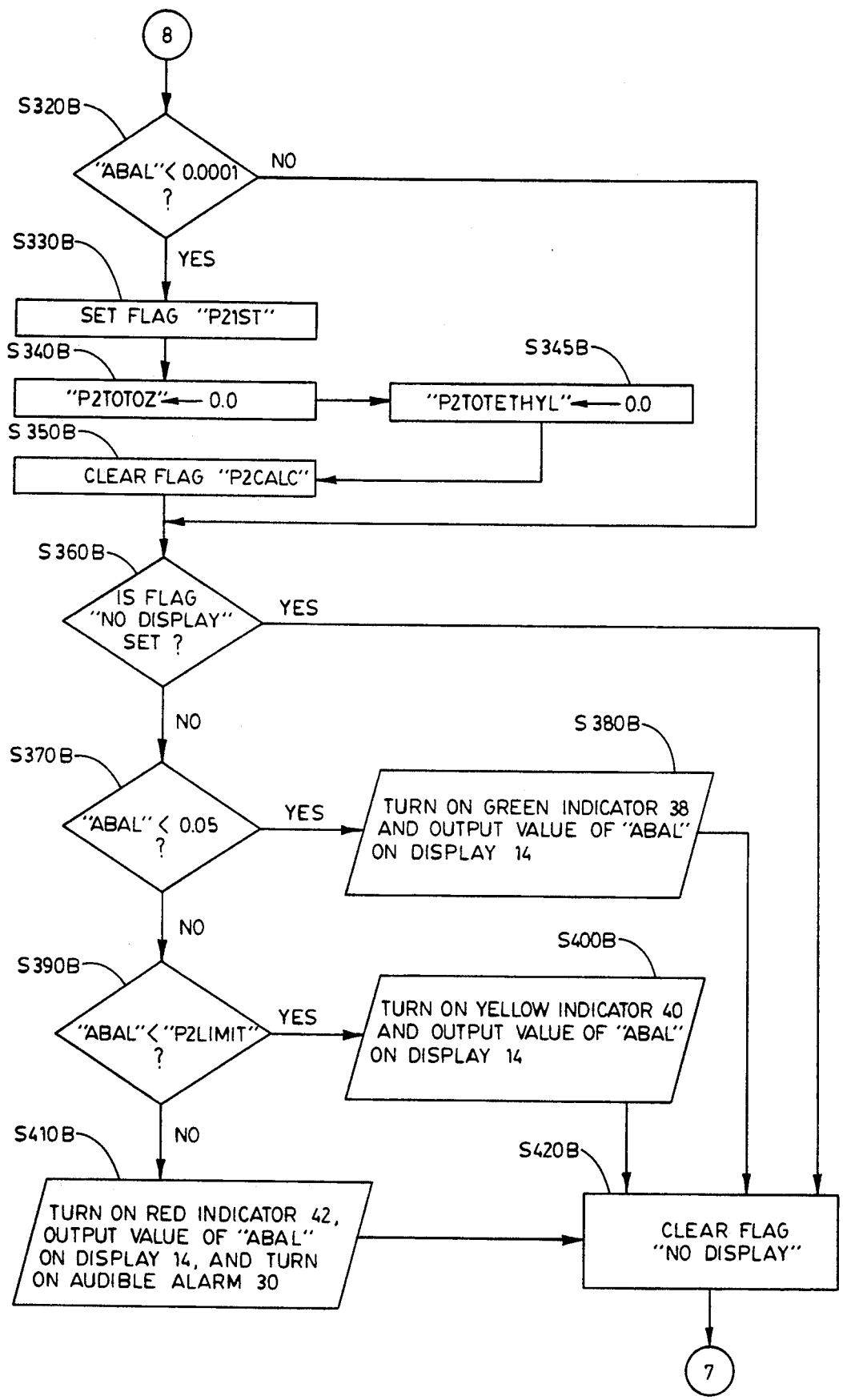

As shown in FIG. 2, the device 10 further comprises a math processor or microprocessor 46 connected to the human interface means 16, the visual indicators 38, 40, and 42, and the audible indicator 30. The device 10 further comprises a display driver 50 connecting the alphanumeric display 14 to the processor 46. The processor 46 further comprises memory 54, and a clock 58.

The processor 46 is connected to the other of the previously described components, and is programmed to interact with those components such that the device 10 functions as will now be described.

When the mode switch 22 is set to the position marked "MATH", the device 10 is in a calculator mode and performs substantially identically to a typical hand held calculator, and the keys marked from "0" to "9", the decimal point key ("."), the addition key ("+"), the subtraction key ("−"), the multiplication key ("×"), the division key ("÷"), the equals key ("="), the add to memory key ("M+"), the subtract from memory key ("M−"), the memory recall/memory clear key ("M$c^R$"), and the display 14 function as they do in a typical hand held calculator having those keys.

When the mode switch 22 is set to the position marked "CLOCK", the device 10 is in a watch mode and provides functions typical of a digital wrist watch. These functions include time of day, alarm, and stopwatch functions.

To set the time of day, after ensuring that the mode switch 22 is in the position marked "CLOCK", a user presses the key marked "SET", and then the key marked "TOD" (which stands for time of day). Next, the user presses various of the keys marked from "0" to "9" to enter the time of day in the format hh.mm.ss (hours, minutes, and seconds) using the 24 hour clock (military) format. Then, the user presses the key marked "=" to start the clock running. The entered time of day will be displayed in the alphanumeric display 14 for five seconds.

To display the time of day, after ensuring that the mode switch 22 is in the position marked "CLOCK", a user presses the key marked "DSP", and then the key marked "TOD". The time of day is displayed in the alphanumeric display 14 for five seconds.

To set the clock alarm, after ensuring that the mode switch 22 is in the position marked "CLOCK", a user presses the key marked "SET", and then the key marked "ALM" (which stands for alarm). Next, the user presses various of the keys marked from "0" to "9" to enter the desired time of the alarm in the format hh.mm.ss (hours, minutes, and seconds) using the 24 hour clock (military) format. Then, the user presses the key marked "=" to complete the setting of the alarm. When the alarm goes off, the audible indicator 30 sounds 15 consecutive times, at one second intervals. A user can press the key marked "=" to turn off the alarm before the end of the fifteen seconds during which it would otherwise sound.

To display the set clock alarm time, after ensuring that the mode switch 22 is in the position marked "CLOCK", a user presses the key marked "DSP", and then the key marked "ALM". The set alarm time is displayed in the alphanumeric display 14 for five seconds.

To set the stop watch, after ensuring that the mode switch 22 is in the position marked "CLOCK", a user presses the key marked "SET", and then the key marked "SS" (which stands for start/stop) to start the stop watch. Elapsed time is displayed in the alphanumeric display 14 in the format hh.mm.ss (hours, minutes, seconds). The user presses the key marked "SS" again, later on, to stop the stop watch, and at that time total elapsed time is displayed in the alphanumeric display 14 for five seconds.

When the mode switch 22 is set to the position marked "ABAL", the device 10 is in a blood alcohol level determining mode and functions as will now be described.

When the mode switch 22 is moved to the position marked "ABAL" from another position, and after the key marked "DRINK" is pressed, blood alcohol level calculations are continuously made, based on information stored in the memory 54, for a first person, if the switch 18 is in the position marked "P1", or for a second person, if the switch 18 is in the position marked "P2". If a calculated blood alcohol level is more than negligible, for example more than 0.0001% (or 0.005% or some other small value), a visual indicator 38, 40, or 42 is turned on, and certain information stored in the memory 54, including information regarding sex and weight of that person, cannot be altered. Only information regarding the characteristics of the alcoholic beverage being consumed by the person can be altered. On the other hand, if the calculated blood alcohol level is negligible (e.g. 0.0001% or less), the blood alcohol level is reset to 0.00%. Information previously stored in the memory 54 regarding the person's weight and sex, the proof level of liquor in the alcoholic beverage being consumed by the person, the number of ounces of liquor in the alcoholic beverage being consumed by the person, and the user selectable predetermined level at which the person is deemed too intoxicated to legally operate a motor vehicle is not changed, although a user of the device 10 can now change the information. (It is to be understood that the term "liquor", as is used herein, encompasses both distilled and fermented liquor; i.e., it is anticipated that the device 10 be capable of use when the first or second person consumes wine or beer instead of a highball or other alcoholic beverage.)

To store, in the memory 54, information regarding the sex of the first person (switch 18 is in the position marked "P1") or regarding the sex of the second person (switch 18 is in the position marked "P2"), if the blood alcohol level for that person was reset to 0.00% and if the mode switch 22 is in the position marked "ABAL", a user of the device 10 first presses the key marked "SET", then the key marked "M/F", and then the key marked "1" if the person is male, or the key marked "2" if the person is a female.

To store, in the memory 54, information regarding the weight of the first person (switch 18 is in the position marked "P1") or regarding the weight of the second person (switch 18 is in the position marked "P2"), if the blood alcohol level for that person was reset to 0.00% and if the mode switch 22 is in the position marked "ABAL", a user of the device 10 first presses the key marked "SET", then the key marked "WGT" (which stands for weight), then various of the keys marked from "0" to "9" to enter weight in pounds, and then the key marked "=".

To store, in the memory 54, information regarding the proof level of liquor contained in the type of alcoholic beverage being consumed by the first person (switch 18 is in the position marked "P1") or regarding the proof level of liquor contained in the type of alcoholic beverage being consumed by the second person (switch 18 is in the position marked "P2"), if the mode switch 22 is in the position marked "ABAL", a user of the device 10 first presses the key marked "SET", then the key marked "PRF" (which stands for proof), then various of the keys marked from "0" to "9" to enter the proof level, and then the key marked "=".

To store, in the memory 54, information regarding the number of ounces of liquor contained in one serving of the type of alcoholic beverage being consumed by the first person (switch 18 is in the position marked "P1") or regarding the number of ounces of liquor contained in one serving of the type of alcoholic beverage being consumed by the second person (switch 18 is in the position marked "P2"), if the mode switch 22 is in the position marked "ABAL", a user of the device 10 first presses the key marked "SET", then the key marked "OZ", then various of the keys marked from "0" to "9" to enter the number of ounces, and then the key marked "=".

To adjust, in the memory 54, the user selectable predetermined blood alcohol level limit at which the first person (switch 18 is in the position marked "P1") or the second person (switch 18 is in the position marked "P2") is deemed too intoxicated to legally operate a motor vehicle, if the mode switch 22 is in the position marked "ABAL", a user of the device 10 first presses the key marked "SET", then the key marked "LIMT" (which stands for limit), then various of the keys marked from "0" to "9" to enter the predetermined blood alcohol level limit, and then the key marked "=". This user selectable predetermined blood alcohol level limit is preset at 0.10%, and can be changed by the user.

In one embodiment of the invention, the processor 46 is programmed to detect unreasonable information input by the user. For example, in such an embodiment, the processor 46 will not permit the user to store a weight of 3000 pounds for the first or second person. As another example, the processor 46, in such an embodiment, will not permit the user to store a predetermined blood alcohol level limit above 0.10% (or whatever the maximum allowable blood alcohol level limit is in the state or province with the highest limit in the country in which the device 10 is being sold).

To display the blood alcohol level calculated for the first person (switch 18 is in the position marked "P1") or for the second person (switch 18 is in the position marked "P2"), if the mode switch 22 is in the position marked "ABAL", a user presses the key marked "DSP". A calculated blood alcohol level is displayed in the alphanumeric display 14 for five seconds. The blood alcohol level is calculated, by the processor 46, based on information stored in the memory 54 regarding the person, and regarding the alcoholic beverage being consumed by the person, and based on elapsed time, kept track of using the clock 58, after the person indicates to the device that a drinking session (involving alcoholic beverages) is about to begin. More particularly, the blood alcohol level is calculated for the person using the following relationship:

$$BAL = ((0.8 \times A)/(W \times R)) - ELIM$$

where BAL is the calculated blood alcohol level; where 0.8 is the approximate specific gravity of alcohol; where A is an amount of ethyl alcohol consumed by the person, in milliliters; where W is the person's weight, in grams; where ELIM is a rate of elimination of alcohol and is presently believed to be $0.015 \times T$ where T is time measured, by the clock 58, from when the person began a drinking session to the present time, in hours; and where R is a distribution ratio and is 0.68 if the person is of male sex, and is 0.55 if the person is of female sex. The value of the rate of elimination (ELIM) changes as scientific understanding changes, and, in one embodiment of the invention, the value used for the rate of elimination is the best value known to science at the time the invention is practiced. Further, the entire blood alcohol level relationship provided above may be modified or changed as scientific understanding changes, and, in one embodiment of the invention, the relationship used is preferably the best relationship known to science at the time the invention is practiced. As will become apparent to one of ordinary skill in the art, any one of various scientifically accepted relationships could be used by the device 10 without departing from the spirit of the invention. Appropriate conversion factors can be used to modify the above blood alcohol level equation (e.g., 30 milliliters per ounce, 454 grams per pound) so that the blood alcohol level equation can be used with standard American measurements.

To indicate to the device 10 that the first person is about to consume a serving of the alcoholic beverage (switch 18 is in the position marked "P1") or that the second person is about to consume a serving of the alcoholic beverage (switch 18 is in the position marked "P2"), if the mode switch 22 is in the position marked "ABAL", a user of the device 10 presses the key marked "DRINK" for approximately one second. To indicate that the input has been accepted, i.e., that the key marked "DRINK" has been pressed for approximately one second, the three visual indicators 38, 40, and 42 will simultaneously blink three times and, at the same time, the audible indicator 30 will beep three times. The blood alcohol level for the person is then calculated by the device 10 using the previously described relationship, after the various variables in the equation are appropriately updated as if another alcoholic beverage has been consumed by the person. If the blood alcohol level calculated for the person is below a first predetermined limit, 0.05% for example, then the green visual indicator 38 is illuminated three times consecutively, and the calculated blood alcohol level is displayed on the alphanumeric display 14 for five seconds. If the blood alcohol level calculated for the person is greater than or equal to the first predetermined level and is below a second predetermined level, 0.10%, for example, then the yellow or amber visual indicator 40 is illuminated three times consecutively, and the calculated blood alcohol level is displayed on the alphanumeric display 14 for five seconds. This second predetermined level is the previously described user selectable predetermined blood alcohol level at which the person is deemed too intoxicated to legally operate a motor vehicle. If the blood alcohol level calculated for the person is greater than or equal to the second predetermined level, then the red visual indicator 42 is illuminated nine times consecutively, the audible indicator 30 is turned on, and the calculated blood alcohol level is displayed on the alphanumeric display 14 for fifteen seconds.

The device 10 further includes a power source (not shown) for supplying power to components of the device 10 that require power to operate, which power source can include any battery type typically used in calculators. Optionally, but preferably, the device 10 further includes a low battery indicator 64 and circuitry that illuminates the indicator 64 if the power source is low on power.

To better enable one of ordinary skill in the art to practice the invention without undue experimentation, a flowchart is provided in FIG. 3 that illustrates one possible sequence of steps that can be programmed into the processor 46, which steps will now be described. In the flowchart of FIG. 3, certain of the above described keys, such as the keys marked "PRF" and "OZ", are eliminated for simplicity, and the information associated with those keys are obtained from the user of the device 10 by way of prompts at the alphanumeric display 14. One of ordinary skill in the art can readily appreciate that the sequence of steps programmed into the processor 46 can easily be modified for inclusion of those keys.

At step S5, a flag, hereinafter referred to as "P11ST" is set to indicate no alcohol has yet been consumed by the first person (or that the blood alcohol level of the first person has dropped over time to a negligible amount). The processor 46 proceeds to step S6 after step S5 has been executed.

At step S6, a flag, hereinafter referred to as "P21ST" is set to indicate no alcohol has yet been consumed by the second person (or that the blood alcohol level of the second person has dropped over time to a negligible amount). The processor 46 proceeds to step S10 after step S6 has been executed.

At step S10, a determination is made as to whether or not the mode switch 22 is in the position marked "ABAL". If so, the processor 46 proceeds to step S60. If not, the processor 46 proceeds to step S20.

At step S20, a determination is made as to whether or not the mode switch 22 is in the position marked "CLOCK" If so, the processor 46 proceeds to step S30. If not, the processor 46 proceeds to step S40.

At step S30, a clock subroutine is called, and conventional clock operations are performed until the switch 22 is moved to a position other than the position marked "CLOCK".

At step S40, a determination is made as to whether or not the mode switch 22 is in the position marked "MATH". If so, the processor 46 proceeds to step S50. If not, the processor 46 proceeds to step S10.

At step S50, a math subroutine is called, and conventional calculator operations are performed until the switch 22 is moved to a position other than the position marked "MATH".

At step S60, a determination is made as to whether or not the key marked "SET" is depressed. If so, the processor 46 proceeds to step S65. If not, the processor 46 proceeds to step S180.

At step S65, a determination is made as to whether or not the switch 18 is in the position marked "P1". If so, the processor 46 proceeds to step S70A. If not, the processor 46 proceeds to step S70B.

At step S70A, a determination is made as to whether or not a flag "P1CALC" is set. (This flag is set in steps that are described below, once consumption of alcoholic beverages has begun by the first person, and this flag remains set until the approximate blood alcohol level for the first person drops, over time, to essentially zero.) If the flag "P1CALC" is set, the processor 46 proceeds to step S135A (only information regarding the proof level of liquor contained in the type of alcoholic beverage being consumed by the first person, and information regarding the number of ounces of liquor contained in the type of alcoholic beverage being consumed by the first person can be changed). If the flag "P1CALC" is not set, the processor 46 proceeds to step S80A.

At step S80A, the processor 46 prompts the user, on the display 14, to enter the sex of the first person for whom an approximate blood alcohol level is to be calculated. The processor 46 proceeds to step S90A after executing step S80A.

At step S90A, the processor 46 inputs the sex (as either 1 for male or 2 for female) into a variable, hereinafter called "P1MF". The processor 46 proceeds to step S92A after executing step S90A.

At step S92A, a determination is made as to whether or not the value of variable "P1MF" is 1 or 2 (whether or not the first person is male or female). If P1MF=1 (the first person is a male), the processor proceeds to step S94A. If P1MF=2 (the first person is a female), the processor 46 proceeds to step S96A.

At step S94A, a variable, hereinafter called "P1RATIO", is assigned the value 0.68. The processor 46 proceeds to step S100A after executing step S94A.

At step S96A, a variable, hereinafter called "P1RATIO", is assigned the value 0.55. The processor 46 proceeds to step S100A after executing step S94A.

At step S100A, the processor 46 prompts the user, on the display 14, to enter the weight of the first person. The processor 46 proceeds to step S110A after executing step S100A.

At step S110A, the processor 46 inputs the weight in pounds into a variable, hereinafter called "P1WGT". The processor 46 proceeds to step S120A after executing step S110A.

At step S120A, the processor 46 prompts the user, on the display 14, to enter the user selectable predetermined blood alcohol level limit for the first person. The processor 46 proceeds to step S130A after executing step S120A.

At step S130A, the processor 46 inputs the user selectable predetermined blood alcohol level limit into a variable, hereinafter called "P1LIMIT". The processor 46 proceeds to step S140A after executing step S130A.

At step S135A, the total amount of ethyl alcohol, in milliliters, consumed by the first person since the start time "P1STIME" is calculated, and is assigned to a variable hereinafter referred to as "P1TOTETHYL", as follows:

$$"P1TOTETHYL" = "P1TOTETHYL" + (("P1PRF") \times (0.5)) \times ("P1TOTOZ" \times 30.)$$

The constant 30 is used in the "P1TOTETHYL" equation to convert U.S. ounces to milliliters. There are two different variables that represent ethyl alcohol consumed by the first person (namely "P1TOTETHYL" and "ETHYL"). The reason for this is that, after step S135A is executed, the user will change the characteristics of the alcoholic beverage being consumed by the first person from previous characteristics. "P1TOTOZ" is then set to ZERO. The processor 46 proceeds to step S140A after executing step S135A.

At step S140A, the processor 46 prompts the user, on the display 14, to enter the proof level of liquor contained in the type of alcoholic beverage being consumed by the first person. The processor 46 proceeds to step S150A after executing step S140A.

At step S150A, the processor 46 inputs the proof into a variable, hereinafter called "P1PRF". The processor 46 proceeds to step S160A after executing step S150A.

At step S160A, the processor 46 prompts the user, on the display 14, to enter the number of ounces of liquor contained in one serving of the type of alcoholic beverage being consumed by the first person. The processor 46 proceeds to step S170A after executing step S160A.

At step S170A, the processor 46 inputs the number of ounces into a variable, hereinafter called "P1OZ". The processor 46 proceeds to step S180 after executing step S170A.

At step S70B, a determination is made as to whether or not a flag "P2CALC" is set. (This flag is set in steps described below for the reasons set forth with regard to flag "P1CALC" in step S70A, above.) If the flag "P2CALC" is set, the processor 46 proceeds to step S135B. If the flag "P2CALC" is not set, the processor 46 proceeds to step S80B.

At step S80B, the processor 46 prompts the user, on the display 14, to enter the sex of the second person for whom an approximate blood alcohol level is to be calculated. The processor 46 proceeds to step S90B after executing step S80B.

At step S90B, the processor 46 inputs the sex (as either 1 for male or 2 for female) into a variable, hereinafter called "P2MF". The processor 46 proceeds to step S92B after executing step S90B.

At step S92B, a determination is made as to whether or not the value of variable "P2MF" is 1 or 2 (whether or not the second person is male or female). If P2MF=1 (the second person is a male), the processor proceeds to step S94B. If P2MF=2 (the second person is a female), the processor 46 proceeds to step S96B.

At step S94B, a variable, hereinafter called "P2RATIO", is assigned the value 0.68. The processor 46 proceeds to step S100B after executing step S94B.

At step S96B, a variable, hereinafter called "P2RATIO", is assigned the value 0.55. The processor 46 proceeds to step S100B after executing step S94B.

At step S100B, the processor 46 prompts the user, on the display 14, to enter the weight of the second person. The processor 46 proceeds to step S110B after executing step S100B.

At step S110B, the processor 46 inputs the weight in pounds into a variable, hereinafter called "P2WGT". The processor 46 proceeds to step S120B after executing step S110B.

At step S120B, the processor 46 prompts the user, on the display 14, to enter the user selectable predetermined blood alcohol level limit for the second person. The processor 46 proceeds to step S130B after executing step S120B.

At step S130B, the processor 46 inputs the user selectable predetermined blood alcohol level limit into a variable, hereinafter called "P2LIMIT". The processor 46 proceeds to step S140B after executing step S130B.

At step S135B, the total amount of ethyl alcohol, in milliliters, consumed by the second person since the start time "P2STIME" is calculated, and is assigned to a variable hereinafter referred to as "P2TOTETHYL", as follows:

"P2TOTETHYL"="P2TOTETHYL"+(("P2PRF")×(0.5))×("P2TOTOZ"×30.)

There are two different variables that represent ethyl alcohol consumed by the second person (namely "P2TOTETHYL" and "ETHYL"). The reason for this is that, after step S135B is executed, the user will change the characteristics of the alcoholic beverage being consumed by the second person from previous characteristics. "P2TOTOZ" is then set to ZERO. The processor 46 proceeds to step S140B after executing step S135B.

At step S140B, the processor 46 prompts the user, on the display 14, to enter the proof level of liquor contained in the type of alcoholic beverage being consumed by the second person. The processor 46 proceeds to step S150A after executing step S140A.

At step S150B, the processor 46 inputs the proof into a variable, hereinafter called "P2PRF". The processor 46 proceeds to step S170B after executing step S160B.

At step S160B, the processor 46 prompts the user, on the display 14, to enter the number of ounces of liquor contained in one serving of the type of alcoholic beverage being consumed by the second person. The processor 46 proceeds to step S170B after executing step S160B.

At step S170B, the processor 46 inputs the number of ounces into a variable, hereinafter called "P2OZ". The processor 46 proceeds to step S180 after executing step S170B.

At step S180, a determination is made as to whether or not, the key marked "DSP" is depressed. If so, the processor 46 proceeds to step S210. If not, the processor 46 proceeds to step S190.

At step S190, a determination is made as to whether or not the key marked "DRINK" is depressed. If so, the processor 46 proceeds to step S210. If not, the processor 46 proceeds to step S200.

At step S200, a flag "NO DISPLAY" is set. This flag allows the processor to cycle through approximate blood alcohol level calculations over time even when the key marked "DRINK" has not been pressed at step S190.

At step S210, a determination is made as to whether or not the switch 18 is in the position marked "P1". If so, the processor 46 proceeds to step S220A. If not, the processor 46 proceeds to step S220B.

At step S220A, a determination is made as to whether or not a "yes" determination was made in step S190; i.e., at step S220A, a determination is made as to whether or not it was determined in step S190 that the key marked "DRINK" was depressed. If a "yes" determination was made in step S190, the processor 46 proceeds, from step S220A, to step 230A. If a "no" determination was made in step S190, the processor 46 proceeds, from step S220A, to step S270A.

At step S230A, a determination is made as to whether or not the flag "P11ST" is set. If so, the processor 46 proceeds to step S240A. If not, the processor 46 proceeds to step S270A.

At step S240A, a variable, hereinafter referred to as "P1STIME" is assigned the present time. The variable "P1STIME" represents the starting time of a drinking session for the first person. The processor 46 proceeds to step S250A after executing step S240A.

At step S250A, the flag "P11ST" is cleared. The processor 46 proceeds to step S260A after executing step S250A.

At step S260A, the flag "P1CALC" is set. The flag "P1CALC" is set to indicate that the key marked "DRINK" was pressed and an approximate blood alcohol level calculation will be made for the first person. The processor 46 proceeds to step S270A after executing step S260A.

At step S270A, a calculation is made of the time that elapsed since step S240A was last performed, and the result is assigned to a variable hereinafter referred to as "P1ETIME". The processor 46 proceeds to step S280A after executing step S270A.

At step S280A, a determination is made as to whether or not a "yes" determination was made in step S190. If a "yes" determination was made in step S190, the processor 46 proceeds, from step S280A, to step 290A. If a "no" determination was made in step S190, the processor 46 proceeds, from step S280A, to step S300A.

At step S290A, a variable, hereinafter referred to as "P1TOTOZ" is incremented by the variable "P1OZ". The variable "P1TOTOZ" represents the total number of ounces of liquor consumed by the first person since the start time "P1STIME", and is initially zero. Since the user indicated, by pressing the key marked "DRINK", that an (another) alcoholic beverage is about to be consumed by the first person, the variable "P1TOTOZ" is incremented by "P1OZ" ("P1OZ" represents the number of ounces of liquor contained in one serving of the type of alcoholic beverage being consumed by the first person). The processor 46 proceeds to step S300A after executing step S290A.

At step S300A, the amount of ethyl alcohol, in milliliters, consumed by the first person since the start time "P1STIME" is calculated, and is assigned to a variable hereinafter referred to as "ETHYL", as follows:

$$"ETHYL" = (("P1PRF") \times (0.5)) \times ("P1TOTOZ" \times 30.) + "P1TOTETHYL"$$

The constant 30 is used in the "ETHYL" equation to convert U.S. ounces to milliliters. The processor 46 proceeds to step S310A after executing step S300A.

At step S310A, the approximate blood alcohol level of the first person is calculated, and is assigned to a variable hereinafter referred to as "ABAL", as follows:

$$"ABAL" = (((0.8) \times ("ETHYL"))/(("P1WGT" \times 454.) \times ("P1RATIO"))) - ((0.015) \times ("P1ETIME"))$$

The constant 0.8 in the "ABAL" equation represents the approximate specific gravity of alcohol. The constant 454 is used in the "ABAL" equation to convert pounds to grams. The product $((0.015) \times ("P1ETIME"))$ in the "ABAL" equation represents the elimination rate, and can be changed if it is determined that a different value for the elimination rate is more appropriate. The processor 46 proceeds to step S320A after executing step S310A.

At step S320A, a determination is made as to whether or not the calculated approximate blood alcohol level "ABAL" for the first person is below a negligible amount such as 0.0001. If so, the processor 46 proceeds to step S330A. If not, the processor 46 proceeds to step S360A.

At step S330A, the flag "P11ST" is set. The processor 46 proceeds to step S340A after executing step S330A.

At step S340A, the variable "P1TOTOZ" is reset to zero. The processor 46 proceeds to step S345A after executing step S340A.

At step S345A, the variable "P1TOTETHYL" is reset to zero. The processor 46 proceeds to step S350A after executing step S345A.

At step S350A, the flag "P1CALC" is cleared. The processor proceeds to step S360A after step S350A has been executed.

At step S360A, a determination is made as to whether or not the flag "NO DISPLAY" is set. If so, the processor proceeds to step S420A. If not, the processor proceeds to step S370A.

At step S370A, a determination is made as to whether or not the approximate blood alcohol level "ABAL" calculated for the first person is lower than 0.05. If so, the processor 46 proceeds to step S380A. If not, the processor 46 proceeds to step S390A.

At step S380A, the green indicator 38 is illuminated, and the approximate blood alcohol level "ABAL" calculated for the first person is output to the display 14. The processor 46 proceeds to step S420A after executing step S380A.

At step S390A, a determination is made as to whether or not the approximate blood alcohol level "ABAL" calculated for the first person is lower than the value of the variable "P1LIMIT". If so, the processor 46 proceeds to step S400A. If not, the processor 46 proceeds to step S410A.

At step S400A, the yellow or amber indicator 40 is illuminated, and the approximate blood alcohol level "ABAL" calculated for the first person is output to the display 14. The processor 46 proceeds to step S420A after executing step S400A.

At step S410A, the red indicator 42 is illuminated, the audible alarm 30 is sounded, and the approximate blood alcohol level "ABAL" calculated for the first person is output to the display 14. The processor 46 proceeds to step S420A after executing step S410A.

At step S420A, the flag "NO DISPLAY" is cleared. The processor proceeds to step S10 after executing step S420A.

At step S220B, a determination is made as to whether or not a "yes" determination was made in step S190; i.e., at step S220B, a determination is made as to whether or not it was determined in step S190 that the key marked "DRINK" was depressed. If a "yes" determination was made in step S190, the processor 46 proceeds, from step S220B, to step S230B If a "no" determination was made in step S190, the processor 46 proceeds, from step S220B, to step S270B.

At step S230B, a determination is made as to whether or not the flag "P21ST" is set. If so the processor 46 proceeds to step S240B. If not, the processor 46 proceeds to step S270B.

At step S240B, a variable, hereinafter referred to as "P2STIME" is assigned the present time. The variable "P2STIME" represents the starting time or a drinking session for the second person. The processor 46 proceeds to step S250B after executing step S240B.

At step S250B, the flag "P21ST" is cleared. The processor 46 proceeds to step S260B after executing step S250D.

At step S260B, the flag "P2CALC" is set. The flag "P2CALC" is set to indicate that the key marked "DRINK" was pressed and an approximate blood alcohol level calculation will be made for the second person. The processor 46 proceeds to step S270B after executing step S260B.

At step S270B, a calculation is made of the time that elapsed since step S240B was last performed, and the result is assigned to a variable hereinafter referred to as "P2ETIME". The processor 46 proceeds to step S280B after executing step S270B.

At step S280B, a determination is made as to whether or not a "yes" determination was made in step S190. If a "yes" determination was made in step S190, the processor 46 proceeds, from step S280B, to step S290B. If a "no" determination was made in step S190, the processor 46 proceeds, from step S280B, to step S300B.

At step S290B, a variable, hereinafter referred to as "P2TOTOZ" is incremented by the variable "P2OZ". The variable "P2TOTOZ" represents the total number of ounces of liquor consumed by the second person since the start time "P2STIME", and is initially zero. Since the user indicated, by pressing the key marked "DRINK", that an (another) alcoholic beverage is about to be consumed by the second person, the variable "P2TOTOZ" is incremented by "P2OZ" ("P2OZ" represents the number of ounces of liquor contained in one serving of the type of alcoholic beverage being consumed by the second person). The processor 46 proceeds to step S300B after executing step S290B.

At step S300B, the amount of ethyl alcohol, in milliliters, consumed by the second person since the start time "P2STIME" is calculated, and is assigned to a variable hereinafter referred to as "ETHYL", as follows:

$$\text{"ETHYL"} = ((\text{"P2PRF"}) \times (0.5)) \times (\text{"P2TOTOZ"} \times 30.) + \text{"P2TOTETHYL"}$$

The constant 30 is used in the "ETHYL" equation to convert U.S. ounces to milliliters. The processor 46 proceeds to step S310B after executing step S300B.

At step S310B, the approximate blood alcohol level of the second person is calculated, and is assigned to a variable hereinafter referred to as "ABAL", as follows:

$$\text{"ABAL"} = (((0.8) \times (\text{"ETHYL"}))/((\text{"P2WGT"} \times 454.) \times (\text{"P2RATIO"}))) - ((0.015) \times (\text{"P2ETIME"}))$$

The constant 0.8 in the "ABAL" equation represents the approximate specific gravity of alcohol. The constant 454 is used in the "ABAL" equation to convert pounds to grams. The product $((0.015) \times (\text{"P2ETIME"}))$ in the "ABAL" equation represents the elimination rate, and can be changed if it is determined that a different value for the elimination rate is more appropriate. The processor 46 proceeds to step S320B after executing step S310B.

At step S320B, a determination is made as to whether or not the calculated approximate blood alcohol level "ABAL" for the second person is below a negligible amount such as 0.0001. If so, the processor 46 proceeds to step S330B. If not, the processor 46 proceeds to step S360B.

At step S330B, the flag "P21ST" is set. The processor 46 proceeds to step S340B after executing step S330B.

At step S340B, the variable "P2TOTOZ" is reset to zero. The processor 46 proceeds to step S345B after executing step S340B.

At step S345B, the variable "P2TOTETHYL" is reset to zero. The processor 46 proceeds to step S350B after executing step S345B.

At step S350B, the flag "P2CALC" is cleared. The processor 46 proceeds to step S360B after step S350B has been executed.

At step S360B, a determinat m as to whether or not the flag "NO DISPLAY" is set. If so, the processor 46 proceeds to step S420B. If not, the processor 46 proceeds to step S370B.

At step S370B, a determination is made as to whether or not the approximate blood alcohol level "ABAL" calculated for the second person is lower than 0.05. If so, the processor 46 proceeds to step S380B. If not, the processor 46 proceeds to step S390B.

At step S380B, the green indicator 38 is illuminated, and the approximate blood alcohol level "ABAL" calculated for the second person is output to the display 14. The processor 46 proceeds to step S420B after executing step S380B.

At step S390B, a determination is made as to whether or not the approximate blood alcohol level "ABAL" calculated for the second person is lower than the value of the variable "P2LIMIT". If so, the processor 46 proceeds to step S400B. If not, the processor 46 proceeds to step S410B.

At step S400B, the yellow or amber indicator 40 is illuminated, and the approximate blood alcohol level "ABAL" calculated for the second person is output to the display 14. The processor 46 proceeds to step S420B after executing step S400B.

At step S410B, the red indicator 42 is illuminated, the audible alarm 30 is sounded, and the approximate blood alcohol level "ABAL" calculated for the second person is output to the display 14. The processor 46 proceeds to step S420B after executing step S410B.

At step S420B, the flag "NO DISPLAY" is cleared. The processor 46 proceeds to step S10 after executing step S420B.

While a preferred embodiment of the invention has been described, various modifications are possible. For example, the labelling and arrangement of keys and switches, and the arrangement and quantity of visual and audible alarms could be different. The sequence in which keys are pressed to enter information could be different. The calculator mode and watch mode could be omitted. Certain keys, such as the keys marked "PRF" and "OZ", could be eliminated, and the information associated with those keys could be obtained from the user of the device by way of prompts at the alphanumeric display 14 (in the manner illustrated in the FIG. 3 flowchart). Arrays or subroutines could be used to avoid duplication of program steps. The units of measure for values entered by the user (e.g. pounds, proof, ounces) could be different, and could include, for example, metric units. Information concerning the first or second person, or concerning the alcoholic beverage being consumed by the first or second person could be programmed into the device by selecting appropriate values from menus containing a variety of values that are preprogrammed into the device. For example, various body weights (110, 120, 130, . . . , 250 lbs) could be preprogrammed into the device and the user of the device could select the appropriate weight for the first or second person using cursor keys. Similarly, information concerning the characteristics (proof level of liquor and number of ounces of liquor, or total amount of ethyl alcohol) of popular alcoholic beverages (e.g. bottle of beer, glass of wine, various cocktails) could be preprogrammed into the device and the user of the device could select the appropriate beverage characteristics using cursor keys. Thus, the scope of the invention is to be limited only by the scope and spirit of the following claims.

I claim:

1. A blood alcohol level determining device for calculating the blood alcohol level of a person, said blood alcohol level determining device comprising:
   first means for storing characteristic information regarding the person;
   second means for storing characteristic information regarding an alcoholic beverage;
   human interface means for receiving, from a human operator of the device, information regarding the characteristics of the person and the characteristics of an alcoholic beverage, said interface means communicating with said first and second means;
   clock means for measuring time;
   means for communicating with said clock means, with said first means, and with said second means, and for calculating a blood alcohol level for the person based on the characteristics of the alcoholic beverage, the characteristics of the person, and time measured by said clock means; and
   means for preventing characteristic information in said first storing means, regarding the person, from being changed unless the blood alcohol level calculated for that person by said communicating and calculating means is below a predetermined level.

2. A blood alcohol level determining device in accordance with claim 1 and further comprising means for indicating the calculated blood alcohol level of the person.

3. A blood alcohol level determining device in accordance with claim 1 and further comprising means for providing an audible alarm if the calculated blood alcohol level of the person exceeds a predetermined level.

4. A blood alcohol level determining device in accordance with claim 1 and further comprising means for providing a visual indication if the calculated blood alcohol level of the person exceeds a predetermined level.

5. A blood alcohol level determining device in accordance with claim 1 and further comprising first indicia means for indicating if the person's blood alcohol level is below a first predetermined level, second indicia means for indicating if the person's blood alcohol level is greater than or equal to the first predetermined amount and less than a second predetermined level, and third indicia means for indicating if the person's blood alcohol level is greater than or equal to the second predetermined level.

6. A blood alcohol level determining device in accordance with claim 4 wherein said first, second, and third indicia means include green, amber, and red visual indicators, respectively, arranged in traffic light order.

7. A blood alcohol level determining device in accordance with claim 1 and further comprising means for making said blood alcohol level determining device capable of operating as a calculator, said blood alcohol level determining device being selectively operable in either a blood alcohol level determining mode, or a calculator mode in which said device operates as a hand held calculator, and said device further comprising user operable switch means for switching between said calculator mode and said blood alcohol level determining mode.

8. A blood alcohol level determining device in accordance with claim 1 and further comprising means, including said clock means for making said blood alcohol level determining device capable of operating similarly to a digital wrist watch and wherein said device is selectively operable in either a blood alcohol level determining mode, or a watch mode in which said device operates similarly to a digital wrist-watch, and said device further comprising user operable switch means for switching between said watch mode and said blood alcohol level determining mode.

9. A blood alcohol level determining device in accordance with claim 1 wherein said communicating and calculating means calculates the blood alcohol level for the person as a function of the person's sex.

10. A blood alcohol level determining device in accordance with claim 1 wherein said communicating and calculating means calculates the blood alcohol level for the person as a function of the person's weight.

11. A blood alcohol level determining device in accordance with claim 1 wherein said communicating and calculating means calculates the blood alcohol level for the person as a function of the number of ounces of liquor in the alcoholic beverage.

12. A blood alcohol level determining device in accordance with claim 11 wherein said communicating and calculating means calculates the blood alcohol level for the person as a function of the proof level of liquor in the alcoholic beverage.

13. A blood alcohol level determining device in accordance with claim 1 wherein said first storing means comprises means for storing characteristic information regarding two persons.

14. A blood alcohol level determining device for extrapolating the blood alcohol level of a person, said blood alcohol level determining device comprising:

first means for storing characteristic information regarding the person;

second means for storing characteristic information regarding an alcoholic beverage;

human interface means for receiving, from a human operator of the device, information regarding the characteristics of the person, regarding the characteristics of an alcoholic beverage, and regarding when an alcoholic beverage is about to be consumed by the person, said interface means communicating with said first and second means;

clock means for measuring time;

means for communicating with said clock means, with said first means, and with said second means, and for calculating a blood alcohol level for the person based on the characteristics of the alcoholic beverage, the characteristics of the person, and time measured, by said clock means, from when the operator indicated that the person was about to consume an alcoholic beverage, said communicating and calculating means calculating the blood alcohol level for the person by performing a calculation employing the following relationship:

$$BAL = ((0.8 \times A)/(W \times R)) - 0.015 \times T$$

where BAL is the calculated blood alcohol level, where A is an amount of ethyl alcohol in the alcoholic beverage, in milliliters;

where W is the person's weight, in grams; where T is time measured, by said clock means, from when the operator indicates to the device that an alcoholic beverage is about to be consumed by the person, in hours; and where R is 0.68 if the person is of male sex, and where R is 0.55 if the person is of female sex;

first indicia means for indicating if the person's blood alcohol level is below a first predetermined level, second indicia means for indicating if the person's blood alcohol level is greater than or equal to the first predetermined amount and less than a second predetermined level, and third indicia means for indicating if the person's blood alcohol level is greater than or equal to the second predetermined level, said first, second, and third indicia means comprising a green, amber, and red visual indicator, respectively, arranged in traffic light order; and means for preventing characteristic information in said first storing means, regarding the person, from being changed unless the blood alcohol level calculated for that person by said communicating and calculating means is below a predetermined level.

* * * * *